United States Patent [19]

Ormsby

[11] 3,932,941
[45] Jan. 20, 1976

[54] ROTATING MACHINE WEAR GAUGE MEANS

[76] Inventor: George S. Ormsby, P.O. Box 8774, Houston, Tex. 77009

[22] Filed: Mar. 27, 1974

[21] Appl. No.: 455,401

Related U.S. Application Data

[62] Division of Ser. No. 223,210, Feb. 4, 1972, Pat. No. 3,849,893.

[52] U.S. Cl. ........... 33/181 R; 33/125 R; 33/169 B; 233/7; 415/118
[51] Int. Cl.² .......................................... G01B 5/14
[58] Field of Search ......... 33/125 R, 174 C, 181 R; 233/7; 415/118

[56] References Cited
UNITED STATES PATENTS

| | | | |
|---|---|---|---|
| 2,394,489 | 2/1946 | Rowe | 33/174 C |
| 2,554,171 | 5/1951 | Brunot et al. | 33/125 R |
| 3,428,247 | 2/1969 | Andresen et al. | 233/7 |
| 3,506,187 | 4/1970 | Kompert et al. | 233/7 |

Primary Examiner—William D. Martin, Jr.
Attorney, Agent, or Firm—Browning & Bushman

[57] ABSTRACT

The present invention relates to detection and measurement of wear in machines having relatively rotating housings and parts such as radially extending blades subject to wear which may exceed a critical degree, and in particular to the measurement and predetermination of wear and of conveyance capacity of a scroll type conveyor. The invention includes the use of a measuring device for measuring the distance between the radially outer edge of a portion of the conveyor blade and a reference point in the housing radially and longitudinally fixed with respect to the axis of the conveyor. This measurement is preferably taken at a predetermined first portion of the blade such that the measurement at said first portion is indicative of the wear and/or conveyance capacity of one or more other portions of the blade.

7 Claims, 7 Drawing Figures

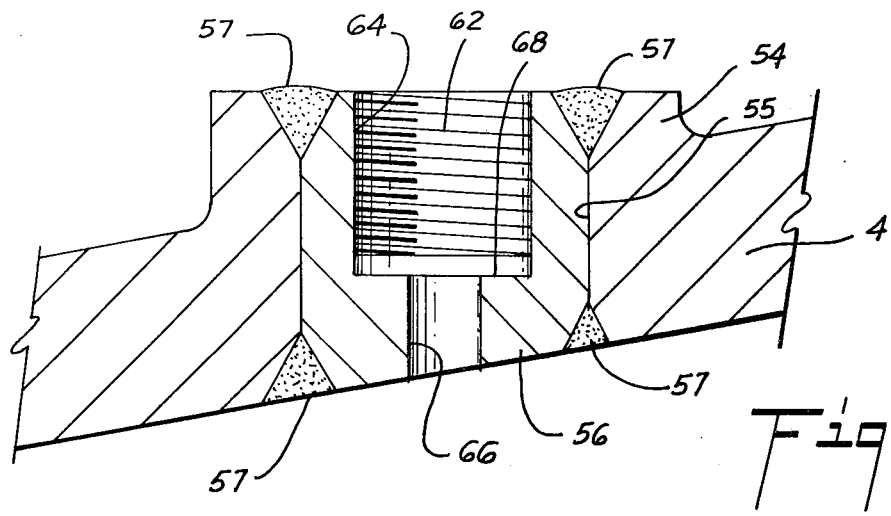
Fig-3
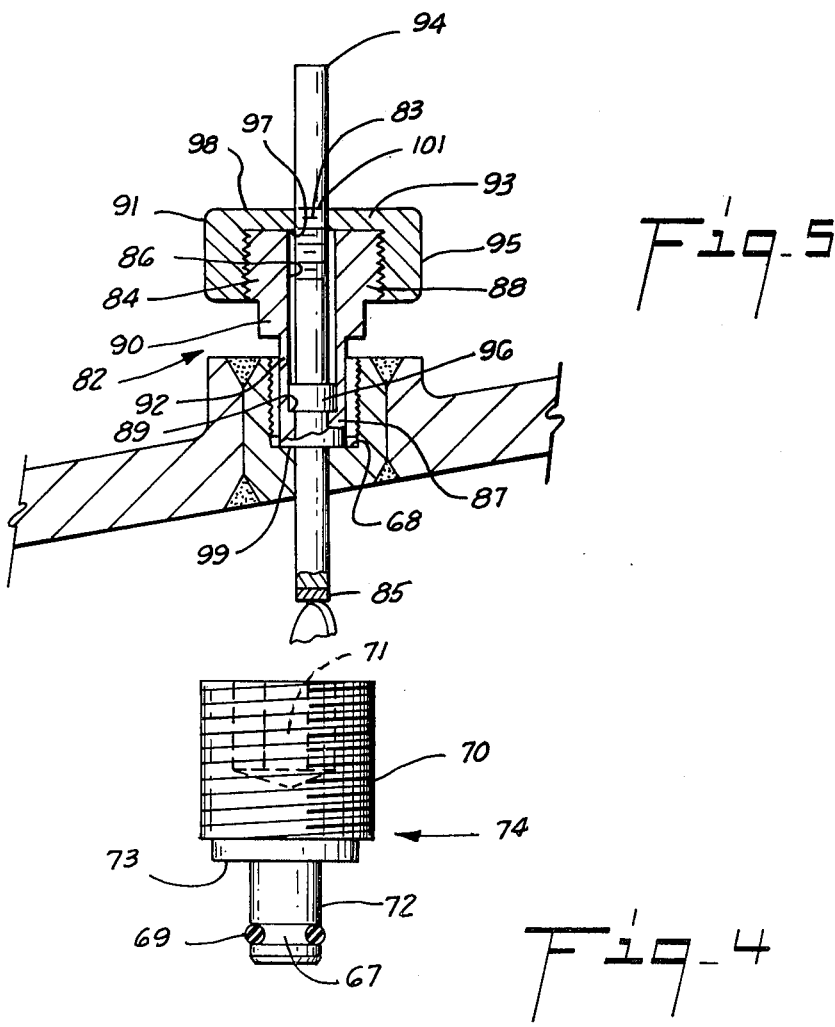
Fig-5
Fig-4

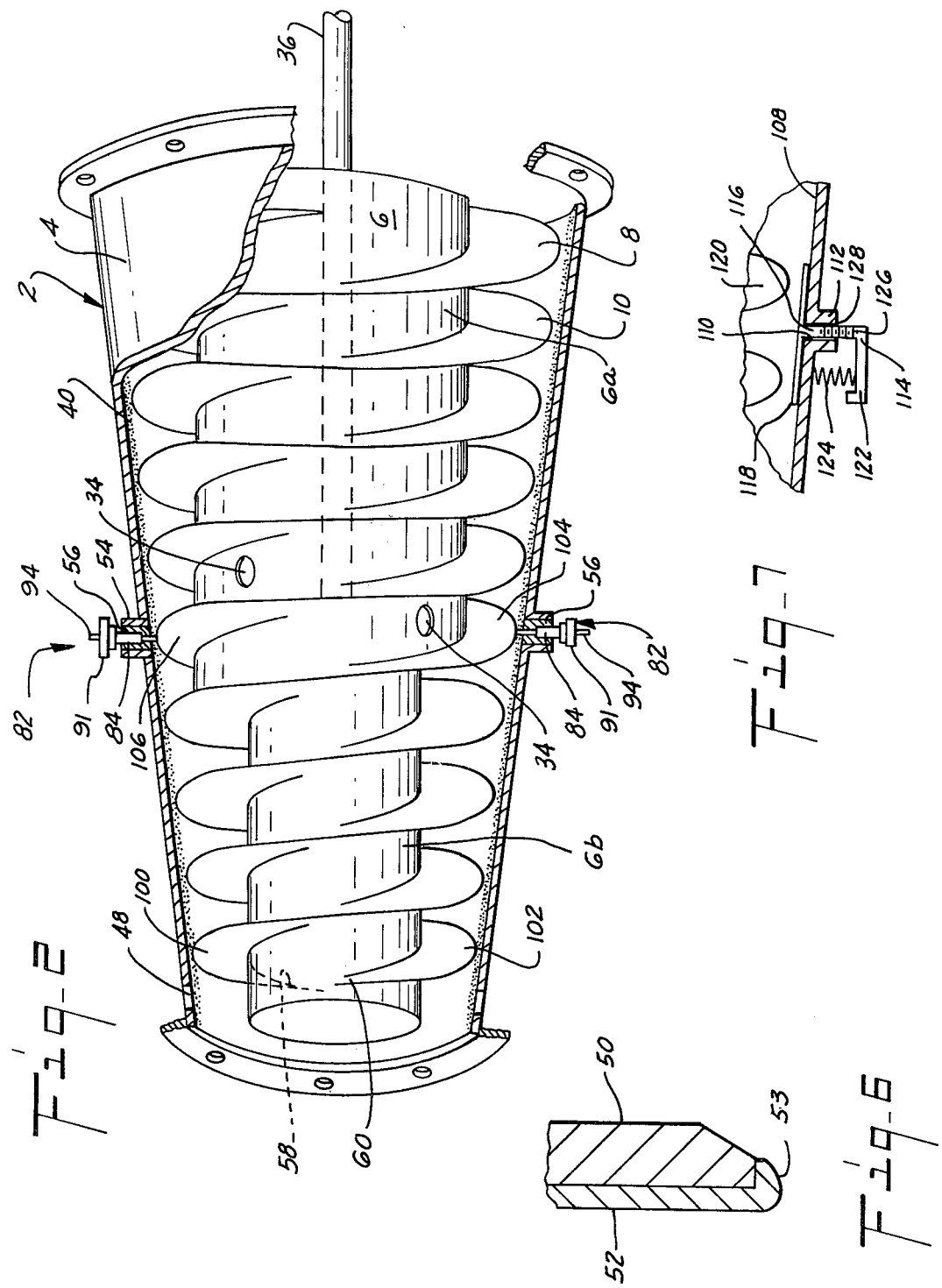

ROTATING MACHINE WEAR GAUGE MEANS

This is a division, of application Ser. No. 223,210, filed Feb. 4, 1972, and now U.S. Pat. No. 3,849,893.

BACKGROUND OF THE INVENTION

The present invention relates to conveyors, detection and measurement of wear in machines having relatively rotating housings and parts such as radially extending blades subject to wear which may exceed a critical degree, and in particlar to scroll type conveyors in which one or more helical blades are carried by a shaft or the like and at least partially encased in a housing.

In order to convey a substance toward one end of the housing, the blade or blades may be rotated within the housing, or the housing may rotate about the blades, or the housing and blades may both rotate at different speeds so that there is relative rotative movement between the blade or blades and the housing.

The outermost edges of the blades of such conveyors wear with use, and while it is desirable to periodically check the degree of wear, this has hitherto necessitated the troublesome, time consuming, and sometimes inaccurate procedure of at least partially disassembling the machine and visually inspecting the blade. The present invention provides a measuring device which may be inserted into an aperture in the conveyor housing to measure the distance between the outer edge of the blade and a fixed reference point. A plug is used to stop the aperture when the conveyor is in operation.

Blade wear can thus be measured by stopping the machine, removing the plug, clearing a path through the adjacent bed of sediment, aligning the blade edge with the aperture, and inserting and operating the measuring device.

In some types of conveyors it might be possible to have a measuring device permanently mounted in the housing wall.

It is, therefore, an object of the present invention to provide a means and method of measuring wear of a conveyor blade while retaining the conveyor in assembled condition.

Such conveyors often have blade wear characteristics which vary along their lengths. A blade may exhibit considerable blade wear along a portion of high wear characteristics while the wear at a second portion of the same blade having low wear characteristics may be so slight as to be very difficult to measure. Yet this second portion of the blade may be of critical conveyance capacity, i.e. slight wear along this second portion may considerably reduce the connveyance capacity of the conveyor as a whole. The present inventor has found that, while wear and conveyance capacity vary along a blade's length, the wear at a first portion of the blade is usually related, so as to be indicative of, the wear and conveyance capacity of other portions. For instance, the wear at various portions may be mathematical functions of the wear at the first portion. If the measuring device of the invention is located adjacent a first portion of the blade, the measurement obtained there can be used to determine the wear at other portions. Preferably the measurement is taken at a first portion of high (and therefore easily measured) wear characteristics, and used to determine or predetermine the wear and/or conveyance capacity at a second, less easily measured portion.

It is therefore a further object of the present invention to provide a means and method for measuring wear at a first portion of a conveyor blade to determine wear and conveyance capacity at a second portion of the blade which may be less readily measurable.

A preferred embodiment of the invention includes a plurality of apertures in the conveyor housing for receiving a plurality of measuring devices. These apertures are equally spaced circumferentially of the housing at a predetermined location along its lengths. This arrangement maintains the balance which is needed, e.g. in centrifuges or other devices in which the housing rotates, and which might be disturbed by the use of a single aperture. In the case of a single blade conveyor, the provision of two or more apertures in the housing reduces the amount of rotation needed to align the blade edge with an aperture. In the case of a multiple lead blade, i.e. a plurality of parallel helical blades arranged about the same shaft, the number of apertures and measuring devices provided is preferably equal to the number of blades. Then when one blade edge is aligned with one aperture, the edges of the remaining blades will be aligned with the other apertures so that all the blades can be checked with the machine in a single position.

It is therefore a further object of the present invention to provide a plurality of measuring devices equispaced about a conveyor housing at a given location along the length of said housing.

Other objects and advantages of the invention will be made evident by the following detailed description and drawings wherein:

FIG. 2 is a view, with parts broken away and parts in cross section, of the conveyor of the centrifuge of FIG. 1 and showing one embodiment of the measuring device in position for use.

FIG. 3 is a cross sectional view of the portion of the housing adapted for reception of the measuring device or the plug.

FIG. 4 is an elevational view of the plug of FIG. 1 on a larger scale with the O-ring shown in cross section.

FIG. 5 is a cross sectional view of the measuring device of FIG. 2 on a larger scale.

FIG. 6 is a cross sectional view of the tip of a conveyor blade.

FIG. 7 is a view partly in section and partly in elevation of a second embodiment of the invention.

Figure 1:
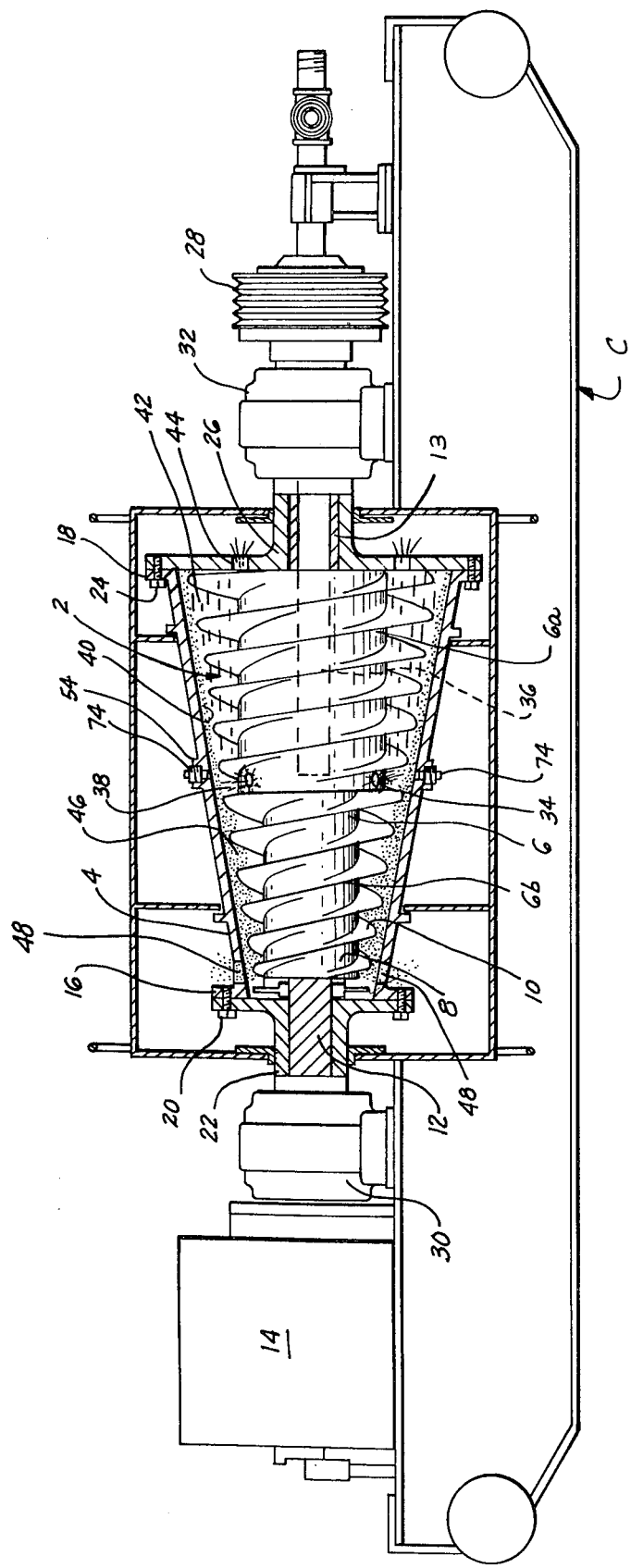
FIG. 1 is a view, partly in section and partly in elevation of a centrifuge-conveyor representing a typical application for the invention.

Referring now to FIG. 1, a centrifuge (represented generally by the letter C) is shown which affords a typical application for the invention. The centrifuge comprises a conveyor 2 having a conical housing or bowl 4. A shaft 6 having a large diameter section 6a and a small diameter section 6b runs through the housing 4, and a pair of parallel helical blades 8 and 10 are carried by the shaft 6. The term "helical" will be used herein to refer to any spiral blade whether its outer diameter is uniform or varying and whether or not the pitch is constant, and the term "parallel" will be used to refer to the blades of multiple lead conveyors regardless of variation in pitch.

The conveyor shaft 6 is suitably connected to an inner drive shaft 12, which is in turn connected to the output of the speed change gear assembly 14, which has its input from the rear outer sleeve shaft 22, to which power is transmitted by the housing 4 from the front outer sleeve shaft 26, which is driven by a motor belted to pulley 28. The housing 4 has integral flanges 16 and 18 at its ends. Flange 16 is connected by bolts 20 to the integral flange of the rear outer sleeve shaft 22. Flange 18 is connected by bolts 24 to the integral flange of the front outer sleeve shaft 26, which is driven by pulley 28. A sleeve shaft 13 is secured to the large end of the conveyor 2 and is rotatably supported in the sleeve 26 to support the large end of the conveyor. Inner drive shaft 12 is supported within rear outer sleeve shaft 22 by sleeve bearings inside shaft 22, and shafts 22 and 26 are supported by suitable bearings 30 and 32.

In operation, a feed, such as a slurry or suspension having a liquid component and solid components, is introduced into the conveyor through feed ports 34 in the shaft 6. The housing 4 is rotated by pulley 28 and sleeve shaft 26 at a sufficient speed so that the feed will be thrown against the inner walls of the housing 4 by centrifugal force. At the same time the blades 8 and 10 are rotated by the gears 14 and drive shaft 12 at a different speed than that of the housing, e.g. the blades and shaft may make 79 revolutions per 80 revolutions of the housing. Thus there is relative rotative motion between the blades 8 and 10 and the housing 4 which causes the blades 8 and 10 of the conveyor 2 to plow or to scrape solid particles toward the smaller end of housing 4 and the conveyor 2.

The feed 38 enters the conveyor shaft 6 through a pipe 36 and flows radially outwardly through feed ports 34 near the center of the conveyor. As the centrifuge rotates, at least the coarser solids are settled to the side walls of the housing 4, and a bed 40 of these solids builds up between these walls and the outer edges of the blades 8 and 10. The fluid component 42 tends to flow into the larger end of the conveyor, and out through fluid ports 44 in the front outer sleeve shaft 26. A relatively dry beach 46 thus forms at the smaller end of the conveyor 2. As more solid particles build up on top of the bed 40, the blades 8 and 10 push them toward the smaller end of the conveyor and out through solid ports 48 in the housing 4.

Because the solids contained in the feed are often of an abrasive character, the edges of the blades become worn. Such wear reduces the conveyance capacity of the blades because the conveyance areas of the blades are reduced and a greater clearance is left between the housing 4 and the edges of the blades 8 and 10. Thus more of the solids are left in the bed and less volume of solids can be conveyed toward the solid ports because the areas of the blades are reduced.

If blade wear progresses to an extreme degree, it is possible for the bed 40 to become so thick at the region of maximum wear that it may form a dam and may interfere with the flow of the liquid toward the fluid discharge ports 44. When this happens, the dammed fluid may be forced out of the solids ports 48, which is an extremely undesirable consequence.

Blade wear is of further concern in connection with maintenance of the machine. As shown in FIG. 6, the tip 50 of a blade may be provided with hard surfacing 52. When the hardsurfacing is worn away from the outer edge 53, the softer material in the tip 50 begins to wear. When this occurs, the blade is much harder to repair.

It is therefore highly desirable to make frequent checks of blade wear in order to determine or predetermine when the blade needs to be changed or repaired either to increase conveyance capacity or to save the blade. This is much more easily done by means of the present invention which eliminates the need for disassembling the machine and makes possible measurements which are quire accurate.

Referring to FIGS. 1, 2, and 3, the housing 4 is adapted to receive either a measuring device or a plug. Housing 4 has a broad annular rim 54 projecting circumferentially thereof from its outer surface with radial bores 55 extending through the housing 4 and rim 54. A cylindrical holder 56 is mounted in the housing 4 within each of the bores 55 by suitable means such as welds 57. While it is possible to practice the invention by providing a single holder, it is preferable in a centrifuge or other machine requiring balance to provide a plurality of holders equally spaced circumferentially of the housing at a given location along its length, i.e. a given distance from one end of the housing. It is also preferable, where the conveyor has a plurality of blades, to make the number of holders equal to the number of blades. In the example shown, there are two blades 8 and 10. Blade 8 has an end 58 (dotted line) located 180° about shaft 6 from end 60 of blade 10. This relationship is maintained throughout the lengths of the blades since they are parallel. Therefore, when one of these blades has its outer edge aligned with one of the two holders 56, the other blade will have its edge aligned with the other holder 56 since holders 56 are located at 180° about the housing from each other.

Each holder 56 has a central aperture 62 having a threaded portion 64 located radially outermost with respect to the conveyor and a smooth inner portion 66 of smaller internal diameter than portion 64 and located radially innermost with respect to the conveyor. A shoulder 68 is located between portions 64 and 66. Shoulder 68 can be parallel to the conveyor axis as shown, or it can be parallel to the housing 4 or disposed at any other angle to the conveyor axis so that a measurement taken normal to shoulder 68 will be proportional to the distance from the blade edge to the housing normal to the housing. When the centrifuge is in use, plugs 74 stop the apertures 62. Each plug 74 has a large externally threaded end 70 for engagement in portion 64 of aperture 62, a small smooth end 72 for engagement in portion 66, and a shoulder 73 for engagement with shoulder 68. An Allen wrench socket 71 is provided in large end 70 to accommodate an Allen wrench for screwing plug 74 into or out of holder 56. A resilient annular O-ring 69 is placed in an annular groove 67 in small end 72 for forming a seal. When suitable housing materials and other housing strength requirements can be met, the geometry of the internal shape of holders 56 can be machined into the parent metal of the housing 4 and broad rim 54 so that separate holders are not needed.

When a blade wear measurement is desired, the feed through pipe 36 is shut off. The conveyor continues to run for a time in order to clear out most of the liquid and solids therein and is sometimes flushed with a clean fluid. The machine is then stopped and the plugs 74 are removed. The bed 40 (FIG. 2) of solids usually remains between the edges of the blades 8 and 10 and the housing 4. Paths are cleared through the bed 40 directly beneath the apertures 62. The shaft 6 is then rotated until the outer edges of the blades are aligned with the apertures 62. A measuring device 82 is inserted in each of the apertures 62.

Each measuring device 82 comprises a carrier 84 with a central bore 86. The carrier 84 has an upper portion 88 which is externally threaded, a short mid portion 90 whose external diameter is slightly less than that of upper portion 88, and a lower portion 92 of even smaller external diameter than that of mid portion 90. An elongated cylindrical probe 94 is slidably carried in the central bore 86. Probe 94 is of uniform diameter throughout its length except for a wide section 96. A scale is provided near the upper end of probe 94, and the lower end may be provided with hardsurfacing 85. The central bore 86 of carrier 84 is of uniform internal diameter, greater than the diameter of wide section 96 of probe 94, throughout portions 88 and 90 and part of portion 92. At the lower end 87 of carrier 84 in portion 92 the internal diameter of bore 86 is reduced so that it is less than the diameter of wide section 96 but larger than that of the other parts of probe 94. An internal shoulder 89 is thus formed in bore 86 which cooperates with wide section 96 to limit radially inward movement of probe 94. The measuring device 82 also includes an annular cap 91 having an upper portion 93 whose internal diameter is less than the width of wide portion 96 but greater than that of the other parts of probe 94. The lower portion 95 of cap 91 is of much larger internal diameter than portion 93 and is internally threaded so that it can be screwed onto portion 88 of carrier 84 after probe 94 has been inserted therein. A shoulder 97 formed between portions 93 and 95 of cap 91 cooperates with wide section 96 of probe 94 to limit outward movement of probe 94. The straight upper surface 98 of cap 91 provides a reference line against which scale 83 can be read.

When the measuring device 82 inserted in aperture 62, the lower edge 99 of carrier 84 rests on shoulder 68. The probe 94 is usually sufficient to clear its own path through bed 40 particularly if its lower end is hard surfaced as at 85 so that it will not become worn and produce inaccurate measurements. When the probe 94 is pushed into the conveyor, it contacts the edge of blade 8 or 10. The scale 83 can then be read with respect to upper surface 98 of cap 91. The reading obtained will be indicative of the distance between the blade edge and a reference point in the housing 4, such as the shoulder 68, which is radially and longitudinally fixed with respect to the conveyor axis. The reading obtained can be compared with a similar reading taken when the blade was new (or some other suitable norm) to determine blade wear. If desired, the scale 83 can be designed to indicate the actual amount of blade wear between successive measurements. To again illustrate a preferred embodiment, FIG. 5 shows that when wide section 96 of probe 94 is resting on shoulder 89 of carrier 84, the top line 101 of scale 83 is aligned with edge 98 of cap 91. Thus line 101 represents the greatest possible extension of probe 94 into the conveyor, and the device 82 can be designed so that line 101 represents the greatest amount of wear tolerable before the blades must be repaired.

It is highly desirable, in producing a number of machines, to arrange the shoulder or shoulders 68 in each machine at given distances from the end of the conveyor and from the conveyor axis and at a given angle with respect to that axis so that measurements taken in the various machines will be standarized regardless of variations in the individual housings.

In conveyors of the type shown in FIGS. 1 and 2, the conveyance capacity of the entire conveyor is usually dependent on the capacity of, and therefore the amount of wear at, portions 100, 102 of the blades nearest the smaller end of the conveyor. Often a slight amount of wear at these portions 100, 102 can greatly reduce the conveyance capacity of the conveyor as a whole, and such a slight amount of wear is often not easily or accurately measurable with simple gauge means such as the measuring device 82 and the cooperating features of the housing 4. However, the present inventor has found that, in many types of conveyors in which conveyance capacity criticality varies over the blade length, blade wear and wear rate also vary over blade length. If the blade wear at a first blade portion can be related as by mathematical functions to wear, rate of wear, and conveyance capacity at other portions of the blade, a blade wear measurement can be taken at the first portion and used to determine amount of wear, rate of wear, or conveyance capacity at one or more other portions, and in particular, a blade wear measurement can be taken at a first portion of high (and therefore easily measured) wear characteristics and be used to determine blade wear at any other portion as well as conveyance capacity at that portion at which conveyance capacity is critical but at which wear characteristics are low and therefore difficult to measure.

For example, in the type of conveyor shown in FIGS. 1 and 2 in which the outer diameter of the blade varies so as to fit a conical housing, and in which feed enters near the center of the conveyor with liquid traveling toward the larger end and solids toward the smaller end, it has been found that while portions 100, 102 of blades 8, 10 have high conveyance capacity criticality and low wear characteristics portions 104, 106 have high wear and low conveyance capacity criticality characteristics. Portions 104, 106 wear rapidly compared to other blade portions, and while this wear is not usually critical to conveyance capacity of the machine, it is critical to the life of the blades.

One wishing to produce a particular conveyor of this type can determine empirically the rates of wear, relative degrees of wear, amounts of wear critical to conveyance capacity, etc. for the various portions of the blades. These values can be related by formulae, curves, charts, graphs, or the like. Then when measurements are taken at portions 104, 106 where wear is easily measured, they can be used to determine wear, conveyance capacity, etc. at portions 100, 102 or any other desired portions. Thus by a single measurement or set of measurements, depending on the number of gauge means employed, one could: (a) determine whether the wear at portions 100, 102 had become sufficient to seriously impair conveyance capacity; (b) determine whether wear at portions 104, 106 had become sufficient to seriously threaten the life of the blade; (c) determine the amount of wear which had occurred at any given portion of the blade. It would also be possible, by means of periodic measurements, to pre-determine the time at which the blades 8, 10 would need repair either to save the blade or to increase conveyance capacity of the machine or to prevent the formation of a dam of solids in the bed. All of these things could be done without disassembling the conveyor. Thus the wear gauge means would be of value to a user who wished to maintain high conveyance capacity as well as to one responsible for maintenance of the machine and desirous of preventing excessive blade wear.

The measuring device of FIGS. 2 and 5 is considered particularly suitable for centrifuge conveyors. However, many other types are possible, and in other types of machines other types of measuring devices might be preferable. It is only necessary that the measuring device permit one to determine the distance from the blade edge at a given portion of the blade length to a fixed reference point without disassembling the machine. For instance, an electronic device could be used which could utilize magnetic flux and electrical current to measure the width of the gap between the housing and blade, the gap being either more or less conductive than the housing and blade.

In some types of conveyors, certainly in those having non-rotating housings, it could be sufficient to provide only one holder and measuring device, particularly if the conveyor had but a single blade. However, even in single blade conveyors with nonrotating housings there is an advantage to the use of several gauges: after the machine is stopped, it might have to be rotated manually in order to align the blade edge with the aperture; if several apertures are provided, less turning of the blade is necessary to align the blade edge with at least one of them.

A further modification might involve a measuring device permanently mounted in the housing of a suitable type of machinery. For instance, as shown in FIG. 7, a housing 108 is provided with an aperture 110 and an outwardly projecting member 112 at the edge of aperture 110. A measuring device 114 is slidably mounted in aperture 110. Measuring device 114 comprises a vertically elongated slide 116. At the inner end of slide 116 is a horizontally elongated shoe 118 of sufficient length so that some part thereof is always aligned with the outer edge of a blade 120. At the outer end of slide 116 is a shoulder 122. A tension spring 124 engages housing 108 and shoulder 122 to bias measuring device 114 outwardly. To take a blade wear measurement, measuring device 114 is pushed inwardly until shoe 118 contacts blade 120; a scale 126 on the slide 116 can then be read with reference to outer edge 128 of member 112.

I claim:

1. In a scroll type conveyor for conveying solids, said conveyor having a helical blade, a housing at least partially encasing said blade and with respect to which said blade has relative rotation, and means defining a feed inlet to said housing and a solids outlet in said housing, said blade having wear characteristics which vary along its length and including a first wear portion and a second wear portion, said first portion having high wear characteristics relative to said second portion, said first portion being closer to said feed inlet than said second portion, and said second portion being closer to said solids outlet than said first portion, the combination of wear gauge means for measuring wear of said blade, said wear gauge means comprising a measuring device in the wall of said housing at a location along the length of said wall which is generally aligned with said first portion of said blade, said measuring device being operable cooperatively with said blade and said housing to measure the distance between a reference point radially and longitudinally fixed with respect to the axis of said blade and the radially outer edge of said first portion of said blade, and wherein the amount of wear of said first portion of said blade is so related to the amount of wear of said second portion of said blade that the amount of wear of said first portion is indicative of the amount of wear of said second portion.

2. The combination of claim 1 wherein said housing has an aperture in said wall at said location and said measuring device is insertable into and removable from said aperture and replaceable by a plug; wherein said measuring device comprises a tubular member insertable into said aperture, and a scaled probe slidably carried by said tubular member and having a lower surface engagable with said outer edge of said blade; and wherein said housing has a stop means in said aperture limiting movement of said tubular member into said housing and positioning it relative to said housing.

3. The combination of claim 2 wherein said tubular member has an index cooperable with the scale of said probe for indicating the position of said probe relative to said tubular member and retaining means for preventing said probe from falling into said housing.

4. The combination of claim 1 wherein said conveyor has a plurality of such blades, said blades being parallel, and said wear gauge means including a plurality of said measuring devices equal to the number of said blades and equally spaced circumferentially of said wall at said location along the length of said wall so that when one of said blades is aligned with one or said measuring devices, each of the remaining blades is aligned with one of the remaining measuring devices.

5. The combination of claim 4 wherein said housing has a plurality of apertures equal to the number of said blades and equally spaced circumferentially of said wall at said location; and wherein said measuring devices are insertable into and removable from said apertures and replaceable by a plurality of plugs equal to the number of said blades.

6. The combination of claim 1 wherein the outer peripheral configurations of said blade and said housing are generally conical and wherein said second portion of said blade is near a small end of said blade.

7. The combination of claim 1 wherein said feed inlet is adjacent the longitudinal mid-portion of said blade.

* * * * *